US00PP08143P

United States Patent [19]

Austin

[11] Patent Number: Plant 8,143

[45] Date of Patent: Feb. 16, 1993

[54] ROSE PLANT—'AUSREEF'

[75] Inventor: David C. H. Austin, Albrighton, England

[73] Assignee: David Austin Roses, Wolverhampton, England

[21] Appl. No.: 623,309

[22] Filed: Dec. 6, 1990

[51] Int. Cl.[5] ..... A01H 5/00

[52] U.S. Cl. ..... Plt./1

[58] Field of Search ..... Plt./1, 21

*Primary Examiner*—Howard J. Locker

*Attorney, Agent, or Firm*—Ladas & Parry

[57] ABSTRACT

A new variety of rose plant of the shrub class, distinctive in its character by its fully double, pale pink flowers which fade to pinkish-white on the outer petals with a hint of yellow at the base of the petals, with abundant continual blooming and the unusual blend of coloring and shaping of the flowers.

1 Drawing Sheet

BACKGROUND OF THE INVENTION

The present invention relates to a new and distinct variety of shrub roses, said new variety originating as a single seedling resulting from a definite effort to produce an improvement in this class of rose.

BRIEF SUMMARY OF THE INVENTION

Primary features of this new variety which connote a distinctive advance over existing types are the vigorous abundant and continual blooming that occurs for 5 months taken with the perfection of the fully double flowers of an old-fashioned shape, more particularly apparent in the accompanying illustration of a specimen thereof.

BRIEF DESCRIPTION OF THE DRAWING

The accompanying illustration shows typical cultivar flowers of this new cultivar in various stages of development, depicted in color as nearly true as is possible to make the same in color illustrations of this character.

DETAILED BOTANICAL DESCRIPTION

The following is a detailed description of the new variety, color terminology being in accordance with the "Methuen Handbook of color" published by Eure Methuen Ltd (1963).

Variety denomination (in accordance with the UPOV Convention): Ausreef.

*Cultivar trade name.*—Sharifa Asma)

*Type.*—Hardy, bush, outdoor, cut flowers, garden decoration.

*Class.*—Shrub.

Propagation: The variety holds its distinguishing characteristics through succeeding propagations by budding.

Asexual reproduction of the new cultivar by budding has taken place at a nursery in Albrighton, Nr. Wolverhampton, England and was derived as follows:

Female parent (seed parent): Mary Rose (non-patented).

Male parent (pollen parent): Admired Mirander (non-patented).

The operation of the artificial pollination is therefore expressed by the following Mary Rose×Admired Mirander.

The following observations are made of specimens grown outdoors in England.

PLANT DESCRIPTION

Plant:

*Height.*—90 cm.

*Habit.*—Bushy, strong.

Branches:

*Young stems.*—Color: 28D8 Deep green. The very longest branches are shaded with violet brown 10EB. Texture: Smooth. Thorns: Numerous, 1–9 mm long. 10D6 brownish red fading to 1B 5 greyish yellow.

*Old stems.*—Color: 28E8 Deep green. Texture: Smooth. Thorns: Numerous 1 mm long. 10E8 violet fading to 7B3 greyish red on underside.

LEAVES

Stipules:

*Length.*—21 mm av.

*Width.*—6 mm av.

*Angle of wingtips to petiole.*—About 45°.

*Color.*—29D8 Deep green shaded with violet brown 10E8.

*Margins.*—Linear or slightly convex, lined with red tipped glandular hairs.

Petiole:

*General description.*—Length: Variable 60–110 mm. Upperside color: 29D8 Deep green variable shaded around groove margins with violet brown 10E8, also at nodes. Groove/hairs/-thorns: Sparsely lined with red tipped glandular hairs. Underside: 29D8 Deep green fading to greyish yellow 1B5 in midline. Hair/thorns: Thorns 2–5 per node. 10C6 brownish red sparse red glandular hairs. Leaflets: Number: 3, 5, 7. Shape: Ovoid with a cuspidate apex and a rounded cordate base. Side somewhat linear, prone to irregularities. Serration: Serrate. Texture: Surface is more or less bumpy, leathery, and dull.

*General effect of foliage.*—Medium dense, dark green (28F7) and semi-glossy.

*Color.*—Young foliage: Upperside: 29E8 Deep green margins with the midrib 10F8 violet brown, and violet brown shading. Underside: 29D8 Deep green with extensive violet brown (10E8) shading more pronounced towards margins. Adult foliage: Upperside: 28F7 Dark green. Underside: 29E6 Spinach green.

INFLORESCENCE

Number of flowers per stem: 1 to 5 (mainly 4).

Pednucle:

*Length.*—Mostly about 70 mm first flower in group of 3 or 4 and has shorter penduncle — about 60 mm.

*Color.*—30D7.

*Thorns/hairs.*—Medium dense red glandular hairs.

Sepals:

*Upperside color.*—29D8 deep green variably streaked with brownish red 10D7.

*Outer margins.*—Occasionally toothed. With sparse red glandular hairs.

*Inner margins.*—Densely tomentose.

*Underside color.*—29D7 Greyish green. Tomentose.

*Sepal length.*—Av. 2.3 mm.

*Bud shape.*—Rounded with cuspidate apex.

*Length.*—27 mm.

*Max. width.*—13 mm.

*Color when opening.*—11C7 Fraise fading to pale orange 5A3.

*Flower shape.*—As a flattened cup. Top flat. Base rounded outer petals recurved towards peduncle.

*Diameter.*—75 mm when blooming.

*Flower color when opening.*—Upperside: Outer petals: Basal tip 2A6 yellow fading to pale rose 11A3. Inner petals: Basal tip 3A7 yellow fading through 3A4 pastel yellow to 10A3 pale red. Underside: Outer petals: Basal tip 2A6 yellow fading to faint rose 11A3 tinge. Inner petals: Basal tip 3A5 light fading pastel yellow to 9A3 pale red.

*Flower color when blooming.*—Upperside: Basal tip 2A7 yellow fading through 2A2 yellowish white to 9A2 pinkish white. Most of petal: Basal tip 2A6 yellow fading to faint rose 11A3. Underside: Basal tip 2A7 yellow fading through 2A3 pale yellow to 9A2 pinkish white. Most of petal: Basal tip 2A6 yellow fading to faint rose 11A3 tinge.

*Flower coloring when finished blooming.*—Upperside: Outer petals: Basal tip 2A4 pastel yellow fading to 11A3 pale rose. Inner petals: Basal 2A3 pale yellow fading through 1A2 yellowish white to a very pale 11A2 pinkish white. Underside: Outer petals: Basal tip 2A2 yellowing white fading to 11A2 pinkish white. Inner petals: Base 2A3 pale yellow fading through white to a very, very pale 11A2 pinkish white.

Length of season of blooming at location of production: From June to October.

Fragrance: Very good, sweet.

Lasting quality: Good.

*Range of days on plant.*—12–14 days.

*Range of days as cut flowers.*—8–12 days.

Petals:

*Shape.*—Outside: Rounded with roughly bilobed top and shoulder cordate apex. Petal cupped, ie. not flat. Middle: Ovate, top broad, rounded, base acute, petal-slightly cupped. Inside: The petal is folded lengthways in half, is heart-shaped, with the base acute and the top bilobed.

*Texture.*—Soft. Outer petals are more leathery.

*Number.*—Av. 90.

*Cleaning.*—Good, drops its petals quickly leaving tidy looking rose.

Stamens:

*Number.*—About 70.

*Anthers.*—Margins dark, golden yellow with paler yellow centers.

*Filaments.*—Irregular heights, yellow at base, with megenta shading towards apex.

Pistils:

*Number.*—About 100.

*Stigmas.*—Straw colored.

*Styles.*—Straw colored hair.

Receptacle:

*Color.*—29D8 Deep green.

*Texture.*—Smooth and glabrous.

*Size.*—Max. width 10 mm. Height 8 mm.

*Shape.*—Goblet shape.

THE DEVELOPMENT

Vegetation: Vigorous.

Blooming: Abundant and continual.

Aptitude to bearing fruits: None.

Resistance to frost: Good.

Resistance to disease: Very good.

I claim:

1. A new and distinct variety of rose plant of the shrub class, characterized as to novelty by its fully double flowers of pale pink which fade to pinkish-white with a hint of yellow at base of petals, with abundant and continual blooming and the unusual blend of coloring and shaping of the flower being substantially as shown and described.

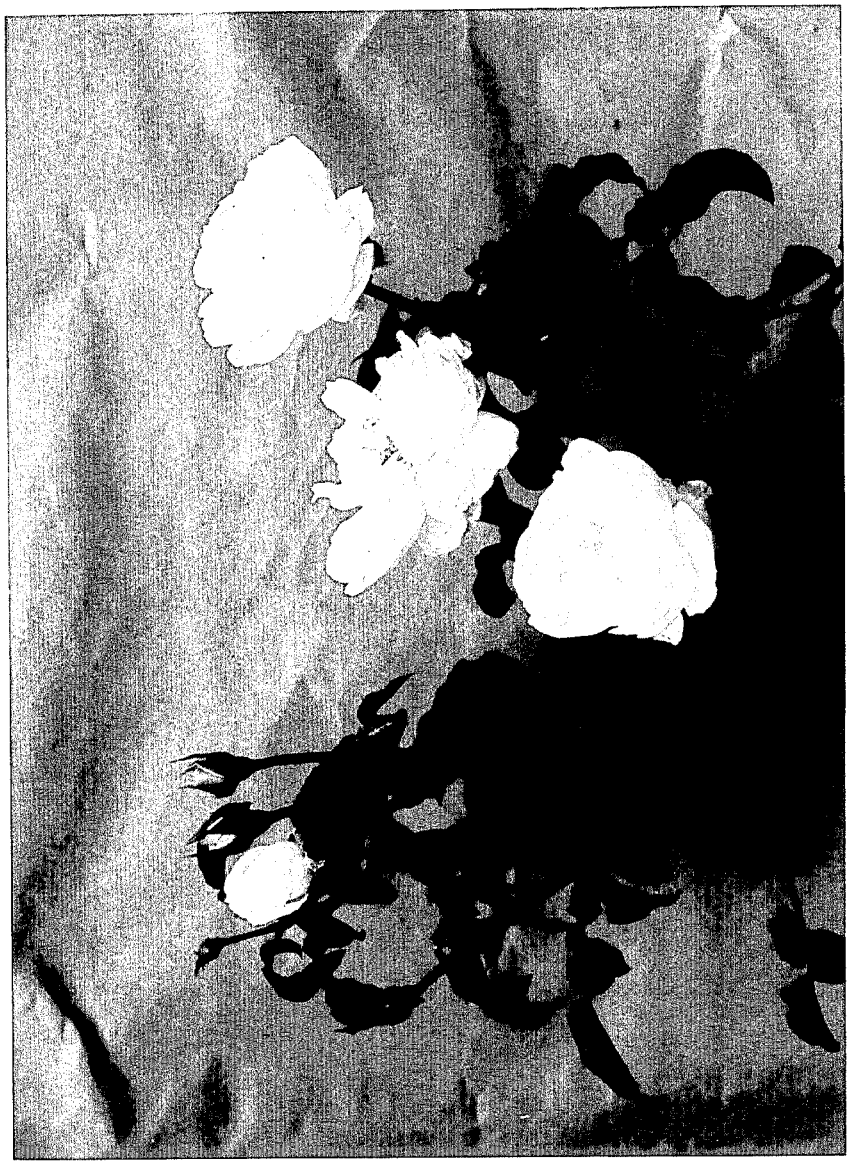

* * * * *